United States Patent
Coleman (10) Patent No.: US 10,682,091 B2
(45) Date of Patent: Jun. 16, 2020

(54) SYSTEM AND METHODS FOR DYNAMIC BONE STRUCTURE INTERACTION

(71) Applicant: Robert Coleman, Cincinnati, OH (US)

(72) Inventor: Robert Coleman, Cincinnati, OH (US)

(73) Assignee: SIGNALYSIS INC., Cincinnati, OH (US)

( * ) Notice: Subject to any disclaimer, the term of this patent is extended or adjusted under 35 U.S.C. 154(b) by 475 days.

(21) Appl. No.: 15/393,487

(22) Filed: Dec. 29, 2016

(65) Prior Publication Data
US 2017/0181688 A1   Jun. 29, 2017

Related U.S. Application Data

(60) Provisional application No. 62/272,389, filed on Dec. 29, 2015.

(51) Int. Cl.
*A61B 5/00* (2006.01)
*A61B 5/11* (2006.01)
*A61B 9/00* (2006.01)

(52) U.S. Cl.
CPC .......... *A61B 5/4504* (2013.01); *A61B 5/0048* (2013.01); *A61B 5/0051* (2013.01);
(Continued)

(58) Field of Classification Search
CPC ... A61B 5/4504; A61B 5/0048; A61B 5/0051; A61B 5/7235; A61B 9/00
See application file for complete search history.

(56) References Cited

U.S. PATENT DOCUMENTS

| | | | | |
|---|---|---|---|---|
| 4,499,906 A | * | 2/1985 | Wohlgemuth | A61B 5/1104 600/589 |
| 5,006,984 A | * | 4/1991 | Steele | A61B 5/417 600/587 |

(Continued)

FOREIGN PATENT DOCUMENTS

WO     8806862 A1    9/1988

OTHER PUBLICATIONS

Collier, R. J., and R. J. Donarski. "Non-invasive method of measuring resonant frequency of a human tibia in vivo part 1." Journal of biomedical engineering 9.4 (1987): 321-328. (Year: 1987).*
(Continued)

*Primary Examiner* — Daniel L Cerioni
*Assistant Examiner* — Raymond P Dulman
(74) *Attorney, Agent, or Firm* — Wood Herron & Evans LLP (57) ABSTRACT

A method of determining a condition of bone structure in a living organism includes impacting a bone to induce vibration in multiple modes having a resonance frequency in a range of about 400 Hz to about 1000 Hz, detecting at least one modal vibration response of the bone for the at least one mode of vibration, and analyzing the at least one modal vibration response to determine a modal vibration characteristic of the bone. A system for determining a condition of bone structure in a living organism includes a force input device configured to impact a bone to induce vibration having a resonance frequency of about 400 Hz to about 1000 Hz, at least one sensor configured to sense at least one modal vibration response, and a computer configured to collect modal vibration response data and analyze the modal vibration response data to determine a vibration characteristic of the bone.

17 Claims, 6 Drawing Sheets

(52) U.S. Cl.
CPC .......... *A61B 5/1104* (2013.01); *A61B 5/4509* (2013.01); *A61B 5/6828* (2013.01); *A61B 9/00* (2013.01); *A61B 5/7235* (2013.01); *A61B 2562/0219* (2013.01)

(56) References Cited

U.S. PATENT DOCUMENTS

| | | | | |
|---|---|---|---|---|
| 5,368,044 | A | * | 11/1994 | Cain .................... A61B 5/4504 600/552 |
| 5,402,781 | A | | 4/1995 | Dimarogonas |
| 5,836,876 | A | * | 11/1998 | Dimarogonas ...... A61B 5/0051 600/407 |
| 5,836,891 | A | * | 11/1998 | Dimarogonas ...... A61B 5/4504 600/552 |
| 2005/0065426 | A1 | | 3/2005 | Porat et al. |
| 2009/0234251 | A1 | * | 9/2009 | Bhattacharya ....... A61B 5/4504 600/595 |
| 2013/0122466 | A1 | * | 5/2013 | Connor ................ A61B 5/0053 433/215 |
| 2016/0058365 | A1 | * | 3/2016 | Bowman .............. A61B 5/4504 600/552 |

OTHER PUBLICATIONS

European Patent Office; Search Report and Written Opinion in International Patent Application No. PCT/US2016/069075 dated Mar. 28, 2017; 20 pages.
Collier et al.; publication entitled "Non-Invasive Method of Measuring Resonant Frequency of a Human Tibia In Vivo Part 1" dated Oct. 1, 1987.

* cited by examiner

SYSTEM AND METHODS FOR DYNAMIC BONE STRUCTURE INTERACTION

CROSS-REFERENCE TO RELATED APPLICATIONS

This application claims the benefit of U.S. Provisional Patent Application Ser. No. 62/272,389 filed Dec. 29, 2015, the disclosure of which is expressly incorporated by reference herein in its entirety.

TECHNICAL FIELD

The present invention relates generally to systems and methods for dynamic bone structure interaction and, more particularly, to systems for determining a condition of bone structure in a living organism and methods of using same.

BACKGROUND

With more than 10 million people affected and 24 million people at risk, osteoporosis has a significant impact on the U.S. healthcare system. Osteoporosis is associated with decreased bone mass and deterioration of the trabecular architecture of the bone, which collectively impact the mechanical properties of the bone. Traditionally, measuring bone mineral density (BMD) has been the predominant diagnostic and screening tool for osteoporosis and other degenerative bone diseases. Currently, dual energy x-ray absorptiometry (DXA) is the most common method of assessing bone density. However, this method is costly. Further, the level of success using the BMD method relies on the validity of a theory that indirectly relates BMD to energy absorption. In other words, no actual energy absorption process is involved with the BMD method. Properties of a bone that manifestly relates to mechanical energy absorption such as vibration damping may be measured instead. In such a case, a theory establishes differential equations of motion that explicitly place bone vibration damping in the role of absorbing energy, and the damping may be directly measured in situ.

The human body is subjected to constant loading and impact during normal daily activities. Among the natural shock absorbers in the human body, trabecular bone has the highest capacity to attenuate incoming shock waves associated with, for example, walking and running. Since osteoporosis is associated with decreased bone mass and deterioration of trabecular architecture of the bone, the disease detrimentally changes the bone's natural shock absorbing capacity.

A conventional procedure for assessing the dynamic bone quality of the trabecular bone involves striking the heel against a force pad and measuring the damping values associated with resonant vibrations in the frequency range of interest. The heel strike induces vibration over the frequency range from about 10 Hz to about 100 Hz (sometimes, but not consistently, extending to 200 Hz). The shock absorption may be quantified by determining a damping ratio of the tibia, which is a measure of the structural integrity of the bone. The damping ratio may be compared to a reference value representing healthy individuals to assess the dynamic bone quality. Generally, a damping ratio that is lower than the reference value indicates a presence or risk of bone disease.

Accurately determining a damping ratio is made difficult due to the vibration of tissue surrounding the tibia. The damping ratio generally used to indicate a healthy tibia is around 35 percent. However, it has been shown that the damping ratio of a healthy tibia without interference from any surrounding tissue is about 10 percent. A metric that includes the effects of surrounding tissue may be representative of the total osteoporosis condition. However, the wide variation within a patient population in the characteristics of tissue surrounding the tibia introduces significant uncertainty in whether the damping ratios produced by conventional procedures adequately represent the dynamic bone quality. Thus, there is an increasing need to provide improved non-invasive, economical tools for accurately assessing and monitoring dynamic bone quality. More particularly, there is a need for improved methods of measuring the damping ratio while the tibia is vibrating in a mode that is decoupled from surrounding tissue (i.e., removed from the influence of surrounding tissue).

SUMMARY

While the invention will be described in connection with certain embodiments, it will be understood that the invention is not limited to these embodiments. On the contrary, the invention includes all alternatives, modifications, and equivalents as may be included within the spirit and scope of the present invention.

In one embodiment, a condition of bone structure in a living organism may be determined in accordance with the principles of the present disclosure. A method of determining a condition of bone structure in a living organism includes impacting a bone to induce vibration in multiple modes having a resonance frequency in a range of about 400 Hz to about 1000 Hz. The method may further include detecting at least one modal vibration response of the bone for the at least one mode of vibration. The method may also include analyzing the at least one modal vibration response to determine a modal vibration characteristic of the bone.

In another embodiment, a system for determining a condition of bone structure in a living organism includes a force input device. The force input device may be configured to impact a bone to induce vibration having a resonance frequency of about 400 Hz to about 1000 Hz. The system may further include at least one sensor configured to sense at least one modal vibration response of the bone associated with the resonance frequency, The system may also include a computer that may be configured to collect modal vibration response data and analyze the modal vibration response data to determine a vibration characteristic of the bone.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
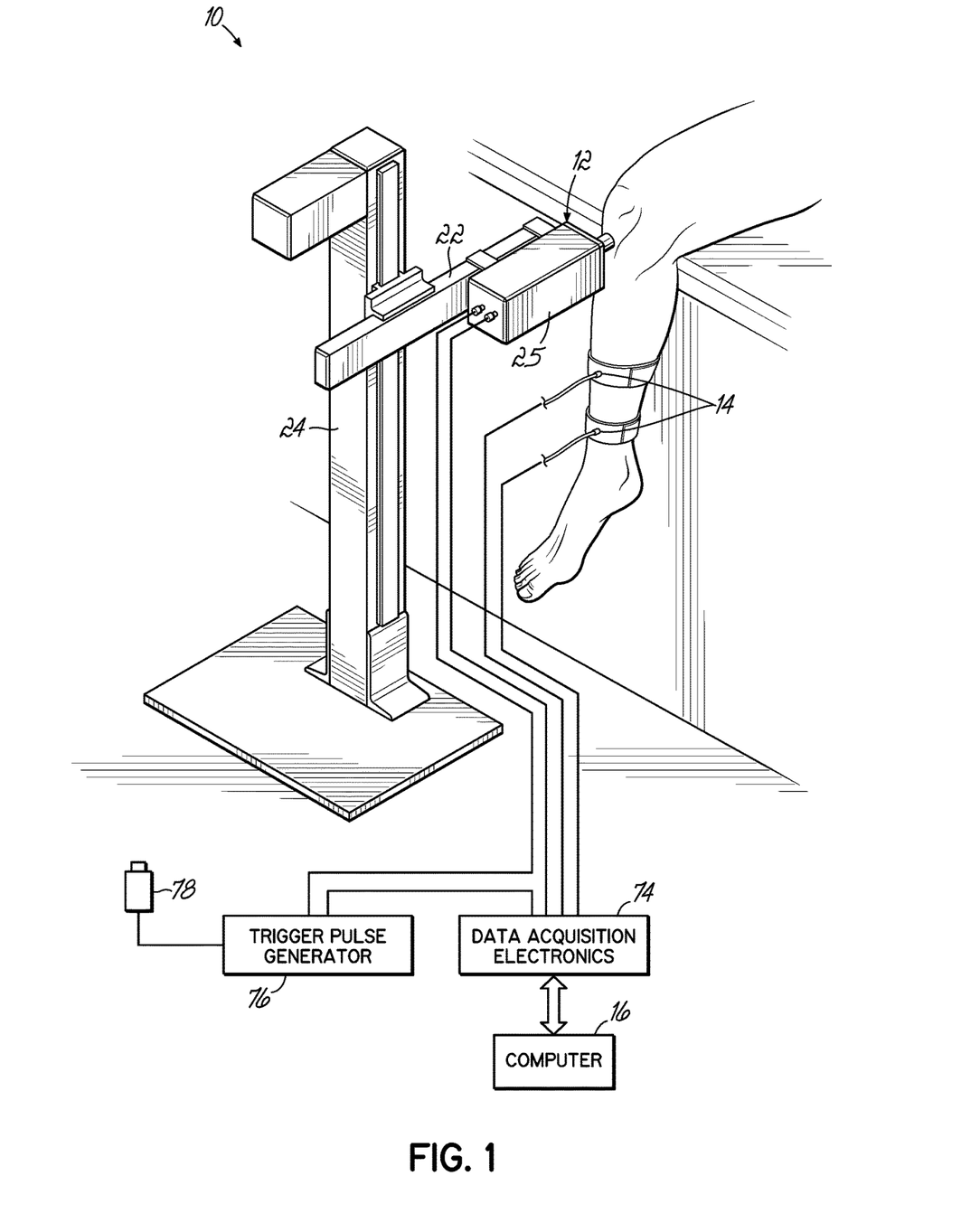
FIG. 1 is a perspective view of an exemplary system for determining a condition of bone structure in a living organism according to one embodiment.

Referring to FIG. 1, an exemplary system 10 for determining a condition of bone structure in a living organism according to an illustrative embodiment is shown. The system 10 includes a force input device 12 and two sensor devices 14. The force input device 12 is configured to apply a force to a bone structure of a living organism, such as a human tibia. The sensor devices 14 measure a response of the bone to the force applied by the force input device 12. The force input device 12 and sensor devices 14 are electronically coupled with a computer 16. The computer 16 is configured to analyze the measured response to quantify the bone shock absorption under dynamic conditions. In one embodiment, the bone shock absorption is quantified by measuring the damping ratio of the bone, which may then be compared to a reference value representing a healthy individual to thereby assess the dynamic bone quality of the subject. Details of the exemplary system 10 are discussed further below.

In one aspect in accordance with the principles of the present disclosure, the system 10 substantially reduces or eliminates interference from the vibration of surrounding tissue during measurement of a response to an applied force. Low frequency bone vibrations are coupled with dynamics of the surrounding tissue, yielding an inaccurate analysis of bone damping properties. Conversely, bone modes of vibration at sufficiently high frequencies provide for dynamic isolation from the surrounding tissue. As discussed above, a resonance frequency of about 100 Hz will result in a damping ratio of about 35 percent for a healthy tibia, while the expected damping ratio of a healthy tibia with no interference from surrounding tissue is about 10 percent. Thus, to measure a damping ratio without tissue interference, the system 10 induces bone vibrations in modes of vibration having resonance frequencies significantly higher than 100 Hz. In one embodiment, inducing bone vibrations in modes of vibration having resonance frequencies in the range from about 400 Hz to about 1000 Hz improves the vibration isolation of the bone from surrounding tissue. The surrounding tissue has a negligible effect on bone vibration damping behavior at sufficiently high frequencies. Inducing bone vibration in the second bending mode having a resonance frequency of about 750 Hz may result in the measurement of about a 10 percent damping ratio. Thus, use of the higher resonance frequency may substantially eliminate the interference of the surrounding tissue.

Figure 2:
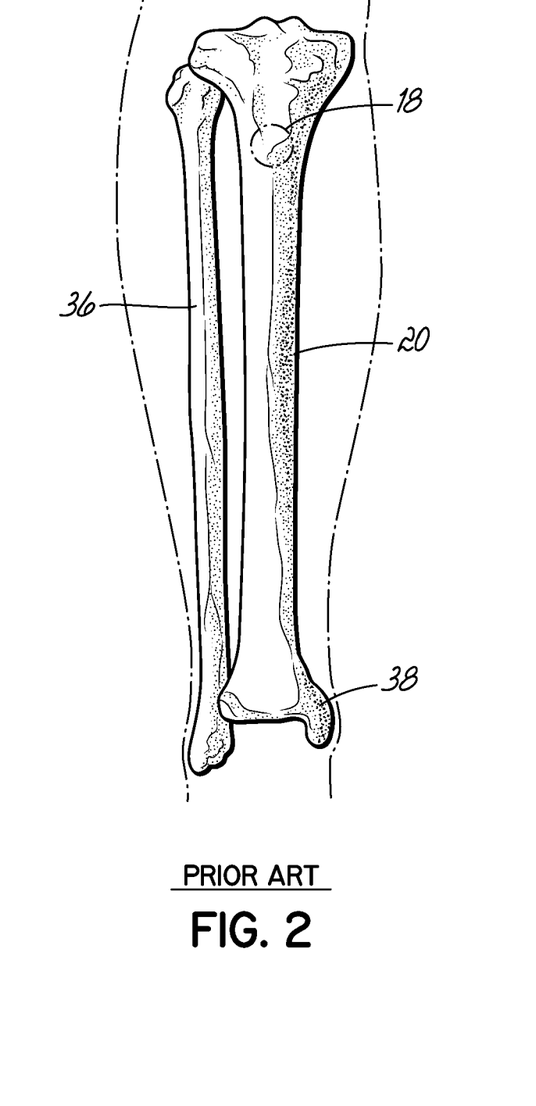
FIG. 2 is an illustrated front view of a tibia and a fibula.

With reference to FIGS. 1 and 2, in another aspect in accordance with the principles of the present disclosure, the force input device 12 of the system 10 is positioned to apply a force to a tuberosity 18 of the tibia 20 to thereby induce the resonance frequency. The resonant mode of vibration having a particular resonance frequency that is being induced in the bone depends, at least in part, on the characteristics of the point of impact of the force. More particularly, the softer the area being impacted is, the lower will be the resonance frequency associated with the induced mode of bone vibration. However, a mode of vibration having a higher resonance frequency may be induced in the tibia by applying the force at a location other than the heel. More specifically, applying the force at an angle that is generally perpendicular to the tibia is greatly more efficient than a vertical heel tap for inducing vibrations with deformation patterns (i.e., mode shapes) associated with the required higher frequencies. The anterior side of the tibia generally includes less tissue between the skin and the bone as compared to the heel. More specifically, the prominence of the tuberosity 18 relative to the skin is generally consistent over a variety of human subjects. Thus, the tuberosity 18 provides a desirable location to apply a force that results in a relatively consistent resonance frequency, independent of the specific anatomy of the individual subject. In other words, applying the force at the tuberosity 18 allows for a consistent patient-to-patient comparison of damping characteristics. It should be recognized that other locations on the body may also be suitable for applying a force resulting in a desirable resonance frequency.

With reference again to FIG. 1, the quality of the response measurement depends, at least in part, on the method of applying the force. To provide accurate response data, any load on the bone should be reduced prior to the force being applied. Moreover, the method of applying the force may be configured to assure maximum dynamic decoupling of the tibia from the femur, which is not possible with a heel strike. To that end, in the illustrative embodiment, the subject being tested is seated with the lower portion of the leg hanging freely downward. In this manner, the response of the bone (e.g., the tibia 20) is not affected by a load from the body weight as compared to a subject that is standing, nor is it affected by strong coupling to the femur. In a related aspect, the force used to induce a resonance frequency may be applied along a direction defining an angle generally perpendicular to the bone. For example, as shown in FIG. 1, the force is applied at a right angle to the tuberosity 18. It will be appreciated that the applied force may alternatively be directed along various other angles, as may be desired or necessary for a given application.

Figure 3:
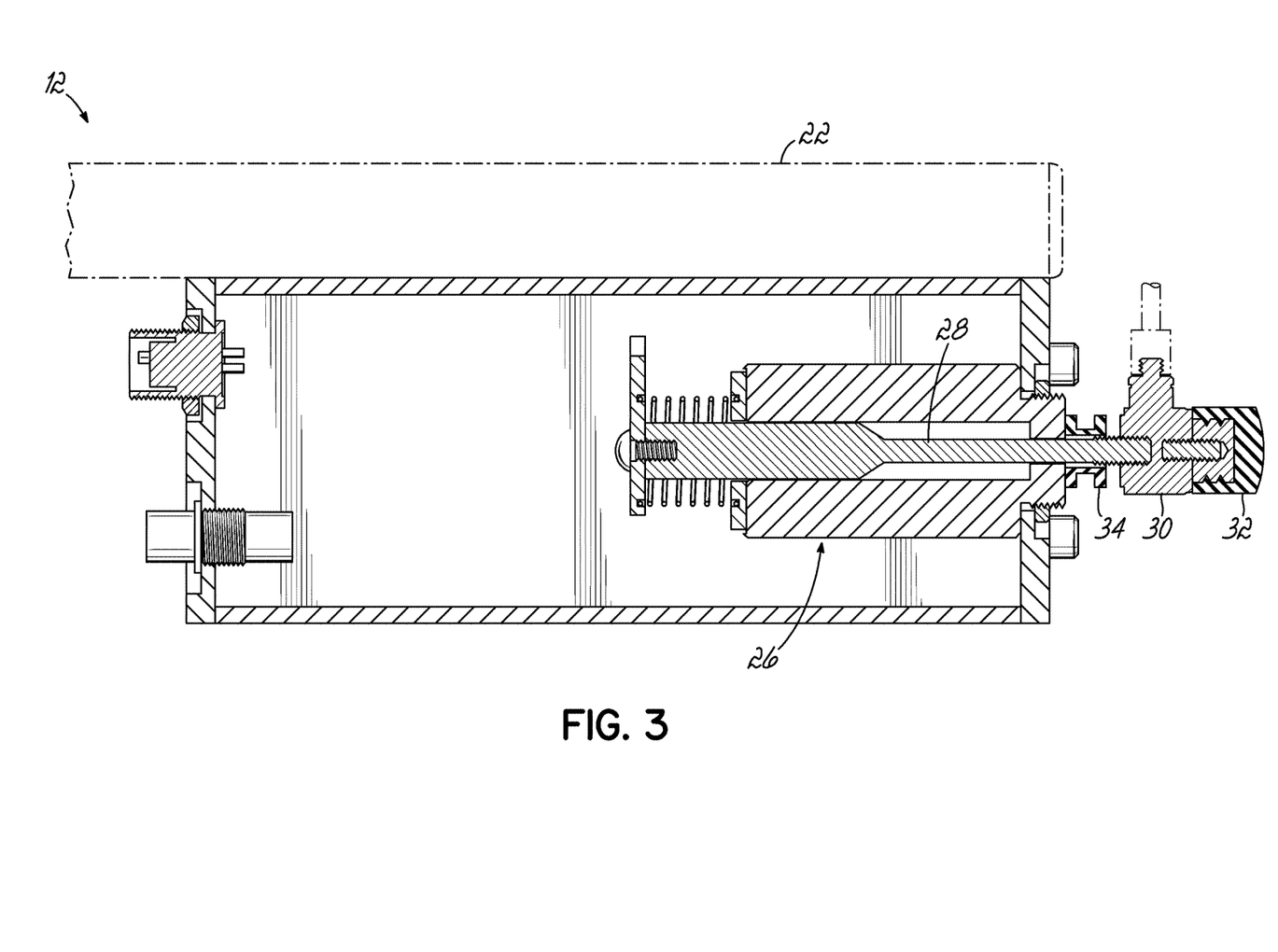
FIG. 3 is a cross-sectional view of an exemplary force input device of the system of FIG. 1.

With continued reference to FIG. 1 and referring further to FIG. 3, the exemplary force input device 12 of FIG. 1 is shown in more detail. The force input device 12 may be coupled to an arm 22, which is slidably coupled to a support post 24. The force input device 12 includes a housing 25, a solenoid 26, and an impact member, illustrated as impact rod 28. In one embodiment, the solenoid 26 may be Model MSA/1334 S-07 166 24 VDC-1D available from Magnet-Schultz of America, Westmont, Ill. A force transducer 30 is coupled to an end of the impact rod 28. A tip 32 may be coupled to the force transducer 30 and is configured to apply the force from the impact rod 28 to the bone. In one embodiment, the tip 32 may be made of plastic. It will be appreciated that various other materials suitable of applying an impact to a bone for dynamic analysis purposes may alternatively be used. When the solenoid 26 is actuated, a magnetic force drives the impact rod 28 from a first, retracted position towards the bone to a second, extended position (not shown). The force transducer 30 measures the force applied to the bone by the impact rod 28. The impact rod 28 extends through a rubber grommet 34, which provides a cushion for the force transducer 30 when the impact rod 28 returns to the retracted position. The dynamic characteristics of the system 10 are designed to provide a sufficiently high resonance frequency required for improved analysis of the dynamic bone quality discussed above. To that end, the force input device 12 is designed to have a relatively low mass and a relatively high stiffness suitable for applying a force transient frequency spectrum that extends beyond 1000 Hz. The tip 32 of the force transducer 30 may be selected using a tradeoff that minimizes peak force (i.e., patient discomfort) and maximizes stiffness with minimum mass. The force required to induce vibration having a desired resonance frequency may vary from patient to patient. In one embodiment, the force applied to the tuberosity ranges from about 9 lbf to about 15 lbf.

In another aspect in accordance with the principles of the present disclosure, the resonance frequency associated with the induced mode of bone vibration depends in part on the method of applying the force. The force should be applied in a single, clean impact on the bone. Accordingly, the mechanism applying the force should rebound directly off the tuberosity 18 without applying a second impact. To that end, the motion or flight of the impact member applying the force should be controlled. With reference again to FIG. 1, in one embodiment, the impact rod 28 is in free flight at the time of contact with the tuberosity 18. In other words, the magnetic force (or other driving force) being applied to the impact rod 28 from the solenoid 26 is removed before the impact rod 28 contacts the bone. The impact from the impact rod 28 in free flight results in a clean excitation of the bone and a desired half sine pulse. If the magnetic force is not removed prior to the impact rod 28 contacting the bone, the magnetic force may continue to direct the impact rod 28 towards the bone after the first strike, thereby resulting in flawed response data. In one embodiment, the impact rod 28 may be in free flight for about two to three milliseconds before impacting the bone.

Figure 4:
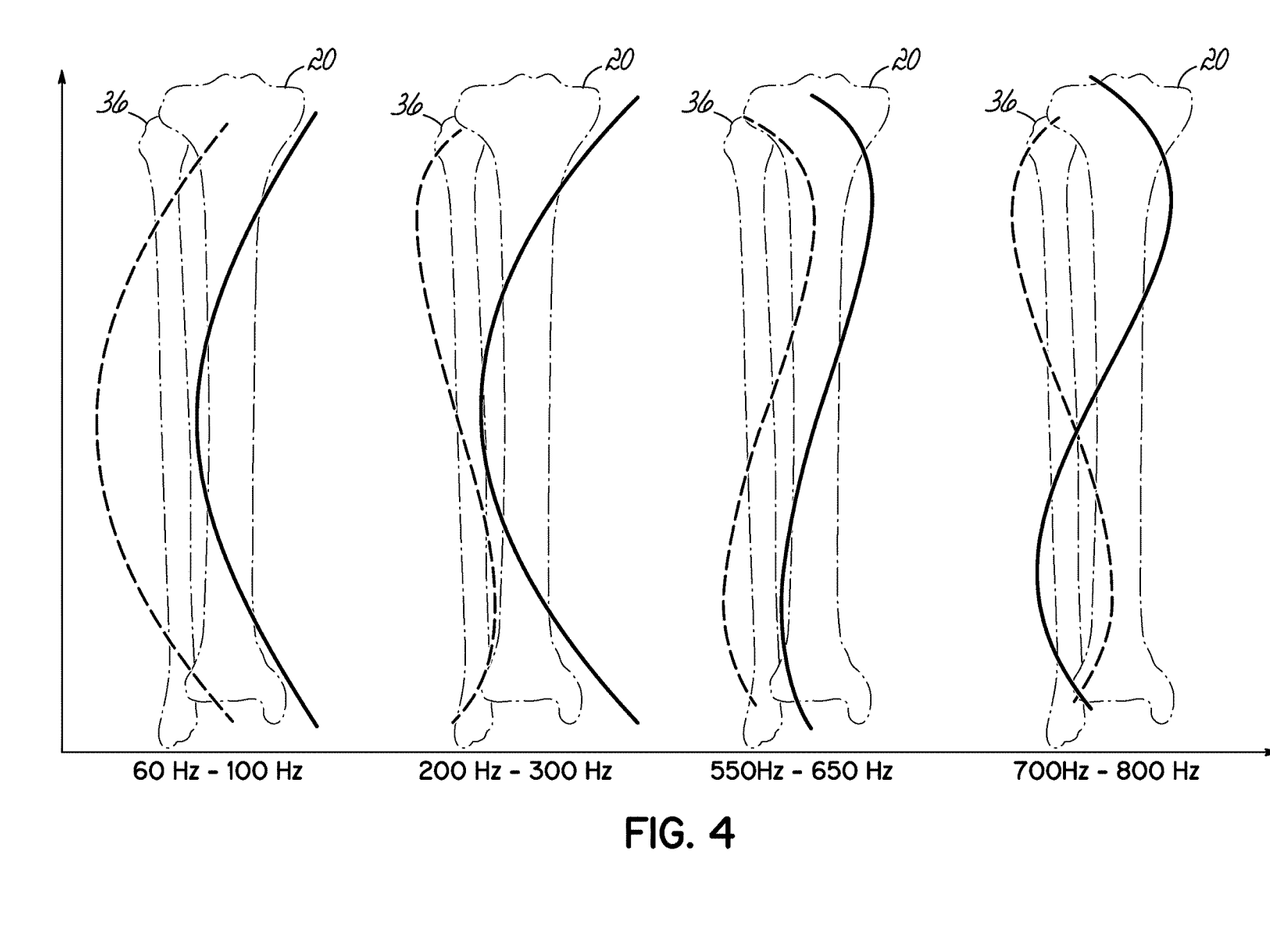
FIG. 4 is a graphical representation of deformation patterns of the tibia and fibula of FIG. 2 due to various resonance frequencies.

Still referring to FIG. 1, the vibration response of the bone due to impact may be measured at one or more locations based on a known deformation pattern (mode shape) of the bone having a known resonance frequency. The perpendicular application of force to the tuberosity 18 induces tibia bending mode vibrations, whereas heel strikes are ineffective as a means of inducing tibia bending mode vibrations due to the soft heel tissue as well as small heel vertical deflections associated with tibia bending modes. The deformation pattern may be mapped by spacing a plurality of accelerometers along the tibia 20 and measuring the response of the bone to an impact. With reference to FIG. 4, illustrative responses (i.e., deformations) of the tibia 20 and the fibula 36 (shown in FIG. 2) are shown in which each deformation is associated with a unique resonance frequency. The bending displacement may be measured in micro-inches. The second bending mode of the tibia 20 is a desirable mode for analysis of damping because it offers better decoupling of vibration of the tibia 20 from vibration of the surrounding tissue and connected structures as compared to the first bending mode. As shown in FIG. 4, the second bending mode of the tibia 20 is prominent in the 600 Hz to 800 Hz range. Notably, the second bending mode may appear at more than one resonance frequency because second bending can occur in combination with two different bending modes of the fibula 36, which is coupled with the tibia 20. Moreover, the bending motion of the tibia 20 may occur in the medial-lateral plane at one frequency and in the anterior-posterior plane at a different frequency. The response may be measured along the length of the tibia 20 between the tuberosity 18 and the medial malleolus 38 (shown in FIG. 2). In one embodiment, the response of the tibia 20 at a resonance frequency in the range of 600 Hz to 800 Hz is generally measured at a first location along the tibia at a distance from the tuberosity 18 that is about 33 percent of the distance between the tuberosity 18 and the medial malleolus 38, and at a second location that is about 69 percent of the distance from the tuberosity 18. The actual distances of the sensor devices 14 from the tuberosity 18 may vary based on the anatomy of a particular patient.

Figure 5A:
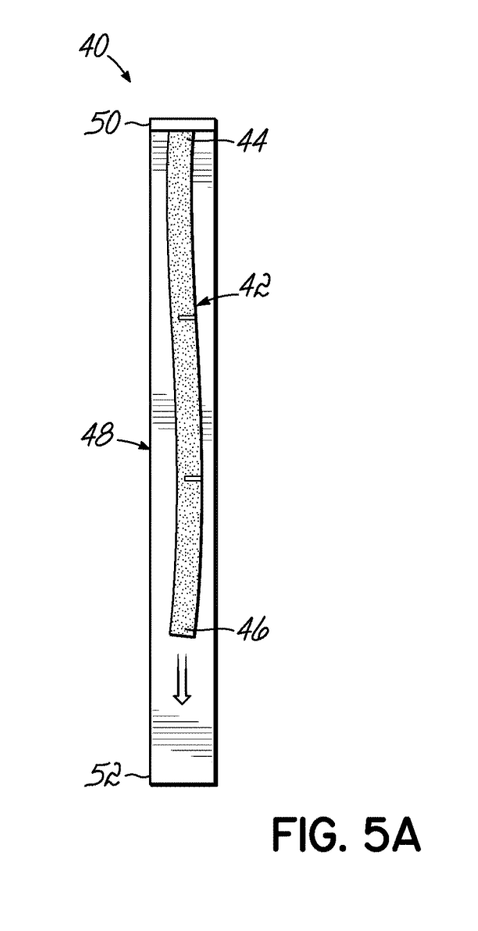
FIG. 5A is a front view of an exemplary adjustable scale according to one embodiment.
Figure 5B:
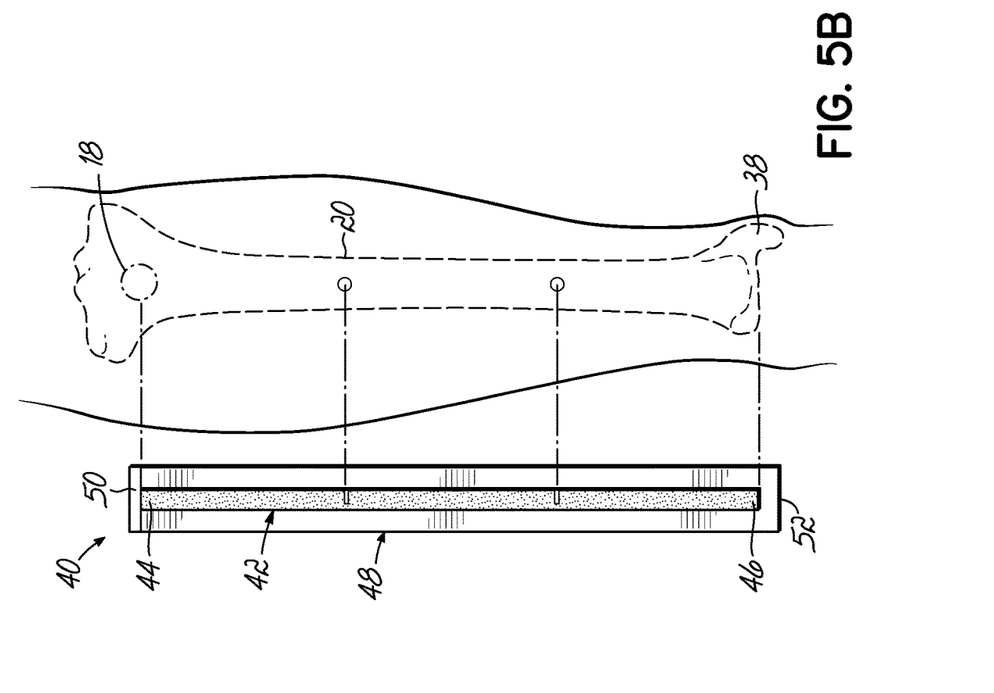
FIG. 5B is a front view of the adjustable scale of FIG. 5A positioned adjacent a human subject.

With reference to FIGS. 5A and 5B, in one embodiment, the sensor devices 14 may be positioned on the subject using an adjustable scale 40. The exemplary adjustable scale 40 includes an elastic band 42 with first and second ends 44, 46 and a rigid frame 48 with first and second ends 50, 52. The first end 44 of the elastic band 42 may be coupled to the first end 50 of the rigid frame 48. One or more locations along the length of the elastic band 42 may be marked to indicate the relative locations at which the response of the bone should be sensed. In one embodiment, the user may desire to position first and second sensor devices 14 at distances from the tuberosity 18 that are about 33 percent and about 69 percent of the distance between the tuberosity 18 and the medial malleolus 38, respectively. Accordingly, one mark is made at a distance from the first end 44 of the elastic band 42 that is about 33 percent of the length of the elastic band 42, and a second mark is made at a distance that is about 69 percent of the length from the first end 44. The rigid frame 48 may be held with the first end 50 positioned adjacent to the subject's tuberosity 18 and the second end 52 positioned adjacent to the subject's medial malleolus 38. In this position, the first end 44 of the elastic band 42 is generally aligned with the tuberosity 18. Next, the elastic band 42 may be stretched so that the second end 46 is generally aligned with the medial malleolus 38. At this point, the marks on the elastic band 42 correspond to the locations along the tibia 20 where the sensor devices 14 are to be positioned, as shown in FIG. 5B. The sensor devices 14 may then be positioned on the tibia 20 according to the marks on the elastic band 42.

Figure 6:
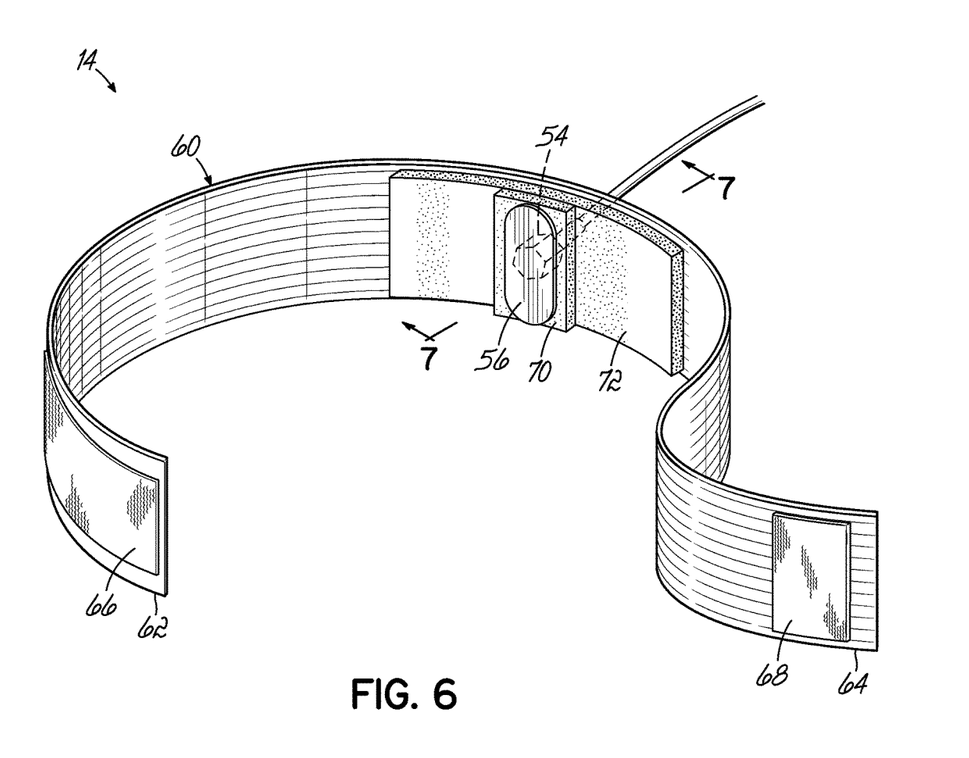
FIG. 6 is a perspective view of an exemplary sensor device of the system of FIG. 1 for measuring a response of the bone to a resonance frequency.
Figure 7:
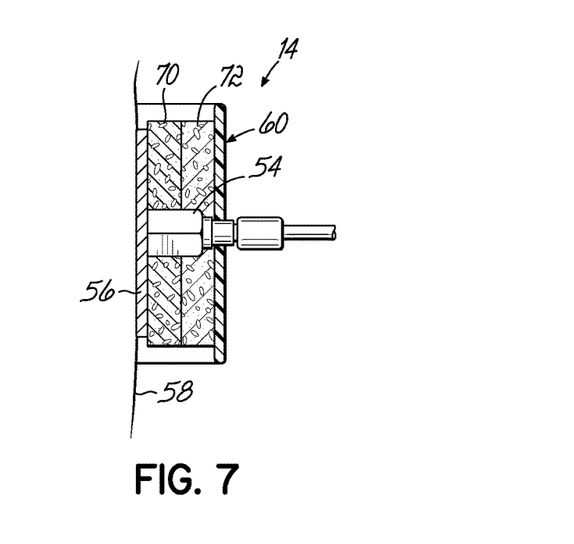
FIG. 7 is a cross-sectional view of the sensor of the system of FIG. 6 taken along the section line 7-7 in FIG. 6.

Referring to FIGS. 6 and 7, an exemplary sensor device 14 is shown in more detail. The sensor device 14 includes an accelerometer 54 coupled to a platform 56. The accelerometer 54 measures the acceleration of the bone in response to the induced resonance frequency. An exemplary accelerometer may be Model 3145A1G, Dytran Instruments, Inc., Chatsworth, Calif., for example. The platform 56 provides stiff local compression between the accelerometer 54 and the skin 58. The sensor device 14 further includes a support, shown in this embodiment as band 60, for securing the sensor device 14 to, for example, the lower leg of a human subject. In one embodiment, the band 60 is elastic and has a very low stiffness relative to the tuberosity 18. The band 60 includes a first end 62 and a second end 64. The first and second ends 62, 64 are configured to be releasably coupled to facilitate adjustment of the band 60 around the leg or other part of a subject's body. In the embodiment shown, the band 60 includes connection pads 66, 68 for coupling the first and second ends 62, 64 together. Connection pads 66, 68 may be made of Velcro®, for example. It will be appreciated that the first and second ends 62, 64 may be adjustably coupled together in various other ways. The sensor device 14 also includes isolation mounts 70, 72 that are provided to sufficiently isolate the accelerometer 54 from the tissue surrounding the bone being analyzed. In one embodiment, the isolation mounts 70, 72 may be made of medium density foam rubber, in which the isolation mount 70 has cross-sectional dimensions of 1.4 in×0.7 in and a thickness of 0.5 in and the isolation mount 72 has cross-sectional dimensions of 1.4 in×3.3 in and a thickness of 0.1 in. Further, in one embodiment, the accelerometer coupling platform 56 is plastic with cross-sectional dimensions of 1.35 in×0.6 in and a thickness of 0.05 in with a rounded end having a 0.4 in tapered radii. The band 60 and the isolation mounts 70, 72 are configured to allow stiff local compression of the accelerometer 54 into the bone without substantially coupling the surrounding tissue to the bone. In other words, the sensor device 14 is designed to measure the response of the bone while reducing interference in the measurement by the response of the surrounding tissue.

With reference again to FIG. 1, the computer 16 may be configured to control the bone testing procedure, to process and store the response data, and to present the results. The computer 16 may be configured to activate the force input device 12 by, for example, sending an electric signal to the solenoid 26. Additionally, the computer 16 may be configured to collect and analyze the signals produced by the force transducer 30 and the sensor devices 14 when the force is applied to the bone by the force input device 12. In one embodiment, the computer 16 utilizes a data acquisition program and a dynamic bone test program. The data acquisition program stores the processed data in a database for use by the dynamic bone test program. The computer 16 may include a user interface for performing the analysis on the measured data using the data acquisition program and a dynamic bone test program. Users, such as doctors or nurses, may be capable of analyzing the dynamic bone quality with little knowledge of structural dynamics technology and with a minimum of training. The computer 16 may be configured to guide the user through the appropriate setup and analysis steps using the user interface. Results may be presented on-screen, and patient reports may be printed. In one embodiment, historical patient data may be stored in a database for later retrieval.

In one embodiment, the data acquisition program communicates with the force transducer 30 and the sensor devices 14 and provides interactive control of relevant signal processing parameters. For example, the data acquisition program may control the channel definition, sample rate, data array size, and time domain windowing. The signals from the force transducer 30 and accelerometers 54 may be digitally sampled into the computer 16 utilizing data acquisition electronics 74 specialized for this purpose, such as analog-to-digital signal sampling and buffering electronics. Additionally, the data acquisition electronics may communicate with a trigger pulse generator 76, which may also be in communication with the force input device 12. The pulse may be activated manually by the operator at the press of a button 78. The button 78 may be, for example, hand-held or mounted to the system 10. The data acquisition electronics 74 may includes an internal potentiometer (not shown) for setting the pulse duration. In various embodiments (not shown), the data acquisition electronics may be packaged as a computer plug-in card or as an external stand-alone electronics module. Those skilled in the art will recognize that the data acquisition electronics may provide analog filtering, appropriate sample rate, and other aspects of signal processing technology to assure adequate frequency response, dynamic range, and the reliable transfer of data from acquisition electronics to computer memory. In addition to digitally sampling the transducer signals, the electronics provide a signal conditioning electrical current to power transducer internal charge converter and buffer amplifier integrated circuits.

In one embodiment, the data acquisition program performs certain pre-processing operations on the raw data. The data acquisition program then performs post-processing to produce, for example, force-time histories, force autospectra, acceleration response vibration time histories, accelerometer response vibration frequency spectra, and frequency response functions (FRFs). The FRFs are presented as either "Magnitude and Phase" or "Real and Imaginary" functions of frequency. The data acquisition program may use force rectangular windowing and acceleration response exponential windowing for noise reduction. The FRFs are used to determine the Laplace domain pole values and/or other significant dynamical parameters.

The dynamic bone test program analyzes the data acquired and processed by the data acquisition program. The dynamic bone test program determines the tibia vibration damping value associated with the induced vibration resonance frequency. The dynamic bone test program is configured to extract the Laplace domain complex poles from the FRF data obtained with the data acquisition program. The FRF data may be analyzed with any of a number of optional methods. Exemplary methods include: 1) the 3 dB-Down Method, 2) the Structural Bandwidth Method, 3) the Impulse Response Function Estimation Method, or 4) the Frequency Domain Estimation Method. Alternatively, Laplace domain complex poles may be extracted from Impulse Response Function (IRF) data produced by performing an inverse Fourier transform on FRF data. In one embodiment, the mathematical model assumed for characterizing the bone dynamics is shown by:

$$H_{pq}(\omega) = \sum_{r=1}^{N} \frac{A_{pqr}}{j\omega - \lambda_r} + \frac{A_{pqr}^*}{j\omega - \lambda_r^*}$$

where: "$\omega$" is a radial frequency in radians/sec; "$H_{pq}(\omega)$" is the FRF as a function of radial frequency; "p" is a numbered location on the bone for measuring the response of the bone; "q" is a numbered location on the bone for inducing the resonance frequency; "r" is a rth mode number of a pole; "$A_{pqr}$ and $A_{pqr}^*$" are a complex conjugate residue pair for locations p and q and mode number r; "$\lambda_r$" is a Laplace domain pole, where $\lambda_r = \sigma_r + i\omega_{dr}$ "$\omega_{dr}$" is a damped resonance frequency for mode number r; "$\omega_r$" is the undamped resonance frequency; and "$\sigma_r$" is an exponential decay exponent. The damping ratio is defined as "$\zeta_r$", where $\zeta_r = \sigma_r/\omega_r$. After the damping ratio is determined, the dynamic bone test program compares the damping ratio to a known, healthy standard to determine the dynamic bone quality.

In one embodiment, the dynamic bone test program uses the Structural Bandwidth ("SB") for computing the damping ratio, $\zeta_r$. For isolated, well defined peaks in the FRF magnitude data (corresponding to resonance frequencies) the "Half Power" point method may be used to obtain the SB. Alternatively, the Real Part of the FRF may be used to extract the SB. To that end, the damping ratio, may be determined by:

$$\zeta_r = SB/(2 \times v_r)$$

where "$v_r$" is the resonance frequency for a selected rth mode of vibration.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A method of determining a condition of bone structure in a living organism comprising:
    impacting a bone with an impact member to induce a vibration in the bone in multiple modes, the vibration having a resonance frequency in a range of about 400 Hz to about 1000 Hz, wherein the impact member is in free flight when the impact member impacts the bone;
    detecting at least one modal vibration response of the bone for the at least one mode of vibration;
    analyzing the at least one modal vibration response to determine a modal vibration characteristic of the bone; and
    determining a damping ratio of the bone using a computer, the computer configured to determine the damping ratio of the bone using the following equation:

$$H_{pq}(\omega) = \sum_{r=1}^{N} \frac{A_{pqr}}{j\omega - \lambda_r} + \frac{A_{pqr}^*}{j\omega - \lambda_r''}$$

where:
    "$\omega$" is a radial frequency in radians/sec;
    "$H_{pq}(\omega)$" is the FRF as a function of radial frequency;
    "p" is a numbered location on the bone for measuring the response of the bone;
    "q" is a numbered location on the bone for inducing the resonance frequency;
    "r" is a rth mode number of a pole;
    "$A_{pqr}$ and $A_{pqr}$" are a complex conjugate residue pair for locations p and q and mode number r;
    "$\lambda_r$" is a Laplace domain pole, where $\lambda_r = \sigma_r + i\omega_{dr}$;
    "$\omega_{dr}$" is a damped resonance frequency for mode number r;
    "$\omega_r$" is the undamped resonance frequency; and,
    "$\sigma_r$" is an exponential decay exponent,
    wherein the damping ratio is defined as "$\zeta_r$", where $\zeta_r = \sigma_r / \omega_r$.

2. The method of claim 1, wherein impacting the bone with the impact member in free flight includes the impact member being in free flight for about 2 to 3 milliseconds before the impact member impacts the bone.

3. The method of claim 1, wherein the bone has a longitudinal axis extending lengthwise along the bone, and wherein impacting the bone includes impacting the bone along a direction defining an angle generally perpendicular to the longitudinal axis of the bone.

4. The method of claim 1, wherein detecting at least one modal vibration response includes detecting at least one modal vibration response at a location on the bone based on a deformation pattern of the bone associated with the resonance frequency.

5. The method of claim 1, wherein detecting at least one modal vibration response includes detecting at least one modal vibration response at a location on the bone corresponding to an anti-node of a deformation pattern.

6. The method of claim 1, further comprising:
    identifying a deformation pattern of the bone associated with the resonance frequency.

7. The method of claim 1, wherein impacting the bone includes impacting a tuberosity of a tibia.

8. The method of claim 7, wherein the tibia has a medial malleolus and a length between the tuberosity and the medial malleolus, and wherein detecting at least one modal vibration response includes detecting a first modal vibration response at a first location about 33 percent along the length of the tibia and a second modal vibration response at a second location about 69 percent along the length of the tibia.

9. The method of claim 1, wherein analyzing the at least one modal vibration response to determine the modal vibration characteristic of the bone includes determining at least one of a damping ratio of the bone, a modal amplitude, a mode coefficient, and the resonance frequency.

10. The method of claim 1, wherein detecting at least one modal vibration response includes detecting an acceleration of the bone.

11. The method of claim 1, wherein the bone has a longitudinal axis extending lengthwise along the bone, and wherein detecting at least one modal vibration response includes detecting a displacement of the bone in a direction generally perpendicular to the longitudinal axis of the bone.

12. The method of claim 1, wherein the vibration has a resonance frequency of about 600 Hz to about 800 Hz.

13. The method of claim 1, wherein the vibration has a resonance frequency of about 650 Hz to about 750 Hz.

14. A system for determining a condition of bone structure in a living organism comprising:
    a force input device including an impact member, the force input device configured to direct the impact member to impact a bone to induce a vibration in the bone, the vibration having a resonance frequency of about 400 Hz to about 1000 Hz wherein the impact member is configured to impact the bone while the impact member is in free flight;
    at least one sensor configured to sense at least one modal vibration response of the bone associated with the resonance frequency; and
    a computer configured to collect modal vibration response data and analyze the modal vibration response data to determine a vibration characteristic of the bone, wherein the computer is configured to determine a damping ratio of the bone using the following equation:

$$H_{pq}(\omega) = \sum_{r=1}^{N} \frac{A_{pqr}}{j\omega - \lambda_r} + \frac{A_{pqr}^*}{j\omega - \lambda_r''}$$

where:
    "$\omega$" is a radial frequency in radians/sec;
    "$H_{pq}(\omega)$" is the FRF as a function of radial frequency;
    "p" is a numbered location on the bone for measuring the response of the bone;
    "q" is a numbered location on the bone for inducing the resonance frequency;
    "r" is a rth mode number of a pole;
    "$A_{pqr}$ and $A_{pqr}^*$" are a complex conjugate residue pair for locations p and q and mode number r;
    "$\lambda_r$" is a Laplace domain pole, where $\lambda_r = \sigma_r + i\omega_{dr}$;
    "$\omega_{dr}$" is a damped resonance frequency for mode number r;
    "$\omega_r$" is the undamped resonance frequency; and,
    "$\sigma_r$" is an exponential decay exponent, wherein the damping ratio is defined as "$\zeta_r$," where $\zeta_r = \sigma_r / \omega_r$.

15. The system of claim 14, wherein the impact member is supported for movement from a first position wherein the impact member is spaced apart from the bone to a second position wherein the impact member impacts the bone.

16. The system of claim 14, wherein each of the at least one sensors includes an accelerometer coupled to an accelerometer platform, a support for securing the sensor to the living organism, and a cushion between the accelerometer and the support.

17. The system of claim 16, wherein the support compresses the accelerometer against a skin adjacent to the bone to allow for measurement of the modal vibration response of the bone without coupling surrounding tissue to the bone.

* * * * *